United States Patent

Kaneko et al.

[11] Patent Number: 6,136,573
[45] Date of Patent: Oct. 24, 2000

[54] PROCESS FOR PRODUCING ALKALI METAL [S,S]-ETHYLENEDIAMINE-N,N'-DISUCCINATES

[75] Inventors: Makoto Kaneko; Takakazu Endo; Toshihiko Fukuda; Mami Kato, all of Yokohama, Japan

[73] Assignee: Mitsubishi Rayon Co., Ltd., Tokyo, Japan

[21] Appl. No.: 09/446,195

[22] PCT Filed: Apr. 15, 1999

[86] PCT No.: PCT/JP99/02003

§ 371 Date: Dec. 17, 1999

§ 102(e) Date: Dec. 17, 1999

[87] PCT Pub. No.: WO99/54492

PCT Pub. Date: Oct. 28, 1999

[30] Foreign Application Priority Data

Apr. 17, 1998 [JP] Japan .................. 10-122721

[51] Int. Cl.$^7$ ..................................... C12P 13/00
[52] U.S. Cl. .................. 435/128; 435/232; 435/280
[58] Field of Search .................... 435/128, 232, 435/280

[56] References Cited

U.S. PATENT DOCUMENTS

| 5,731,468 | 3/1998 | St. George et al. | 562/565 |
| 5,874,262 | 2/1999 | Zahner et al. | 435/128 |
| 5,981,238 | 3/1998 | Kaneko et al. | 435/106 |

FOREIGN PATENT DOCUMENTS

| 9-140390 | 6/1997 | Japan . |
| 10-52292 | 2/1998 | Japan . |
| 10-271 999 | 10/1998 | Japan . |
| 11-9294 | 1/1999 | Japan . |

*Primary Examiner*—Herbert J. Lilling
*Attorney, Agent, or Firm*—Oblon, Spivak, McClelland, Maier & Neustadt, P.C.

[57] ABSTRACT

A process for producing an [S,S]-ethylenediamine-N,N'-disuccinic acid alkali metal salt which comprises reacting fumaric acid with ethylenediamine in an aqueous medium in the presence of an ion of at least one metal selected from the group consisting of alkaline earth metals and transition metals by the action of ethylenediamine-disuccinic acid ethylenediamine lyase of microorganism origin, adding an alkali hydroxide to a reaction product mixture thereby to separate and recover the metal ion as an insoluble precipitate, and obtaining an [S,S]-ethylenediamine-N,N'-disuccinic acid alkali metal salt.

6 Claims, No Drawings

PROCESS FOR PRODUCING ALKALI METAL [S,S]-ETHYLENEDIAMINE-N,N'-DISUCCINATES

This application is a 371 of PCT/JP99/02003 filed Apr. 15, 1999

TECHNICAL FIELD

The present invention relates to a process for producing [S,S]-ethylenediamine-N,N'-disuccinic acid alkali metal salts by the action of ethylenediamine-N,N'-disuccinic acid ethylenediamine lyase of a microorganism origin. The present invention also relates to the above-mentioned process in which a metal ion added to a reaction mixture for the purpose of improving a reaction yield is recovered and reused.

BACKGROUND ART

The present inventors have previously found a novel lyase of microorganism origin which catalyzes a reaction of converting fumaric acid and ethylenediamine into [S,S]-ethylenediamine-N,N'-disuccinic acid (hereinafter abbreviated as SS-EDDS) and the like (said lyase is hereinafter designated as ethylenediamine-N,N'-disuccinic acid ethylenediamine lyase and abbreviated as EDDS-ase) and proposed an efficient process for producing optically active aminopolycarboxylic acids from fumaric acid and various amines which makes use of the catalytic action of the enzyme with various microorganisms (cf. JP-A-9-140390).

However, it has been revealed that although the reaction of producing optically active aminopolycarboxylic acids, such as SS-EDDS, by EDDS-ase is accompanied by only a very slight degree of side reactions, it is an equilibrium reaction and hence leaves a substantial part of starting materials unreacted. Thereupon, the present inventors have found that by making polyvalent metal ions present in the reaction mixture, the reaction equilibrium can be shifted to the product side nearly to complete the reaction and resultantly a marked improvement of the yield can be attained (cf. JP-A-10-52292 and JP-A-10-271999).

The present inventors have further confirmed that though the SS-EDDS formed, in the reaction mixture after nearly completion of the above-mentioned reaction (the reaction mixture is hereinafter referred to as reaction product mixture), is dissolved by forming a complex with the co-existing polyvalent metal ion, it can be easily recovered by crystallization using a mineral acid in the form of crystals of SS-EDDS containing no metal ions. However, the acid-precipitated SS-EDDS is difficult to be soluble in water and, in order to make it easily soluble to widen its field of application, it is necessary to convert it into a monovalent metal salt. Such monovalent metal salts can be obtained by adding an alkali, such as sodium hydroxide, to the SS-EDDS recovered by acid precipitation after reaction, but this method requires an increased number of process steps and hence is complicated.

Moreover, even when the metal compound is recovered by acid precipitation as the salt of the mineral acid, a neutralization with an alkali is necessary for reusing it thus obtained, and resultantly it comes to have a high salt concentration and a problem occurs that the salt unfavorably accumulates successively as the recycle is repeated. Furthermore, it has been confirmed that when the high concentration solution is added as a metal ion source to a reaction mixture comprising fumaric acid, ethylenediamine, alkali, etc., a precipitate which is assumed to be a fumaric acid salt is apt to be formed. Thus, it is difficult that this method can be regarded as a practical means for reusing the metal salt.

Moreover, in order to shift the above-mentioned reaction equilibrium sufficiently to the product side and thereby to obtain a satisfactory yield, it is necessary to use a metal compound of nearly equal mole to the SS-EDDS formed. Such a metal compound, however, ordinarily contains much insoluble matters other than the metal compound. Therefore, in using the compound in practice, it is necessary to use it after purification or to use an expensive purified product.

Accordingly, the object of the present invention is to efficiently produce alkali metal salts of SS-EDDS, taking into consideration the reaction velocity, yield, operation, cost and other factors.

DISCLOSURE OF THE INVENTION

The present inventors have made extensive study to attain the above-mentioned object. As the result, the inventors have found that by conducting a reaction in the presence of a specific metal ion and by adding, after the reaction, an alkali hydroxide to the reaction product mixture, the metal ion present as SS-EDDS-metal complex in the mixture can be separated and recovered as an insoluble precipitate and an SS-EDDS alkali metal salt can be easily obtained and further that the precipitate obtained above can be used in the reaction for producing the SS-EDDS alkali metal salt, and have attained the present invention.

Thus, the present invention provides a process for producing an [S,S]-ethylenediamine-N,N'-disuccinic acid alkali metal salt which comprises reacting fumaric acid with ethylenediamine in an aqueous medium in the presence of an ion of at least one metal selected from the group consisting of alkaline earth metals and transition metals by the action of ethylenediaminedisuccinic acid ethylenediamine lyase of microorganism origin, adding an alkali hydroxide to a reaction product mixture thereby to separate and recover the metal ion as an insoluble precipitate, and obtaining an [S,S]-ethylenediamine-N,N'-disuccinic acid alkali metal salt.

It is surprising that in spite of the fact that SS-EDDS has at the center of its molecular structure an amino group which shows a property of forming a firmer complex under alkaline conditions, the metal ion is rapidly released to form a precipitate which is assumed to be a hydroxide or oxide and the SS-EDDS alkali metal salt is easily formed by adding the alkali into a solution of an SS-EDDS-metal complex. The precipitate can be easily recovered in a high yield and can be reused for the SS-EDDS production reaction without being subjected to desalting and purification.

BEST MODE FOR CARRYING OUT THE INVENTION

The microorganism pertaining to the present invention and the method for cultivation thereof are described below.

The metal ion used in the present invention is not particularly restricted so long as it coordinates to SS-EDDS and, by adding an alkali hydroxide, becomes insoluble and precipitates, and may be, for example, the ions of alkaline earth metals and transition metals. More specifically, it may be an ion (including complex ion) of Fe(II), Fe(III), Mn(II), Mg(II), etc. The sources of these metal ions may be, for example, hydroxides, oxides, and salts of inorganic or organic acids, such as sulfuric acid, hydrochloric acid, phosphoric acid, carbonic acid and acetic acid, of these metals, and further minerals containing these metal compounds and compounds of these metals with fumaric acid or ethylenediamine, which are the substrates of the present invention. These compounds may also be used as a mixture of two or more kinds thereof.

Though some of these metal compounds have only a low solubility in water or are hardly soluble in water, they are usable in the present process because even when they exist in an amount larger than a saturation amount for example in the state of suspension, a substantial part thereof is solubilized by a coordinating function of SS-EDDS.

Generally, SS-EDDS is produced by bringing the above-mentioned metal compound, fumaric acid and ethylenediamine into contact in an aqueous medium (e.g., water, buffer solution) with strain cells of the microorganism described later or with a substance obtained by treating the strain cells (for example, disrupted strain cells, strain cell extract, an extracted crude or purified enzyme, immobilized strain cells or enzyme, and strain cells or enzyme subjected to a treatment with chemicals (e.g., stabilizing treatment)), but it can also be produced by adding the metal compound, fumaric acid and ethylenediamine directly to a culture broth of the strain cells.

When the EDDS-ase according to the present invention is applied to the reaction, it is usually subjected beforehand to a treatment for removing fumarase activity present in the cell. A pH for the treatment is in the range of from 8 to 10.5, preferably from 8.5 to 10, a treating temperature is usually in the range from freezing temperature to 55° C., and a period of time of the treating is not particularly limited (cf. JP-A-9-311046).

The reaction is conducted in the temperature range of usually from 5 to 60° C., preferably from 10 to 55° C. A pH at the time of the reaction is in the range of from 4 to 11, preferably from 6 to 10. A concentration of fumaric acid used in the reaction, though it varies depending upon the reaction temperature and the pH, is usually in the range of from 0.01 to 3M; the presence of the acid as a precipitate due to its concentration exceeding the saturation solubility is permissible because the precipitate goes into a solution with a progress of the reaction. A concentration of ethylenediamine is usually from 0.01 to 2M. The amount of the metal compound added to the reaction mixture is usually from 0.01 to 2 times by mole relative to the SS-EDDS to be formed. The amount of the microorganism or the like used is usually from 0.01 to 5% by weight, in terms of dry strain cells, based on the amount of the substrate.

After the reaction, the strain cells or the substance obtained by treating the strain cells are removed by a filtration, a centrifugation, etc. and an alkali hydroxide, such as sodium hydroxide and potassium hydroxide, is added to it until the metal ion becomes insoluble. The SS-EDDS alkali metal salt can be obtained as a supernatant by removing the insolubilized precipitate by conventional means for a solid-liquid separation, such as a filtration and a centrifugation.

The amount of the alkali hydroxide used is from 2 to 6 times by mole, preferably from 3 to 4.5 times by mole, relative to the SS-EDDS contained in the reaction mixture though it varies depending upon the kind of the metal ion used in the reaction. The alkali hydroxide may be used either singly or as a mixture of two or more kinds thereof, or in combination with other alkalis.

In adding the alkali hydroxide, when it is added at once in a short period of time, a precipitating insolubilized product tends to be fine particles and difficult to separate; but an addition over a sufficiently long period of time is preferable because particles with good sedimentation property are obtained thereby. Both when the alkali is added to the reaction product mixture or, conversely, when the reaction product mixture is added to the alkali, a solidification will take place at the instant when the liquid drop added comes into contact with the other liquid, so that an uniformity in the vessel tends to be hardly maintained, the particle diameters tends to be not uniform, and fine particles tend to be formed. As a more recommendable procedure for such a case, the reaction product mixture and the alkali hydroxide are fed together into a suitable crystallization vessel and, preferably, the simultaneous feeding and an extraction of a slurry from the vessel are conducted continuously, whereby relatively large particles of improved separability can be obtained.

Thus, according to the above-mentioned operations, an aqueous solution of SS-EDDS alkali metal salt can be obtained. The aqueous solution of SS-EDDS alkali metal salt obtained according to the present invention contains little of organic impurities since the reaction for the production thereof proceeds with a high yield and a high selectivity, so that the supernatant obtained after removing metallic precipitates therefrom can be used, as it is, as an industrially useful SS-EDDS alkali metal salt; but, if necessary, it can be purified with ion exchange resins or the like. Further, if necessary, crystals of SS-EDDS alkali metal salt can be obtained by concentrating, solidifying or spray drying the aqueous solution, and crystals of SS-EDDS can be obtained by adding a mineral acid.

The recovered precipitate of the metal compound can be used for the reaction for producing SS-EDDS by being mixed again with the reaction mixture containing fumaric acid and ethylenediamine. In this instance, for example when the reaction is carried out in the presence of magnesium ions, pH decreases during the reaction; but in such a case, the precipitate of magnesium (assumed to be hydroxide or oxide) recovered by the above-mentioned operation may also be used as an alkali for keeping the pH constant during the reaction.

The reactions and recovery operations described above may be conducted either batch-wise or continuously.

The microorganism pertaining to the present invention may be any desired one so long as it is a microorganism having an EDDS-ase activity.

Examples thereof include bacteria belonging to any of the genus Burkholderia, the genus Acidovarax, the genus Pseudomonas, the genus Paracoccus, the genus Sphingomonas and the genus Brevundimonas, and transformants obtained by introducing a gene DNA which codes EDDS-ase into bacteria belonging to the genus Esherichia or the genus Rhodococcus which serve as a host.

Specific examples include Burkholderia sp. KK-5 (FERM BP-5412), Burkholderia sp. KK-9 (FERM BP-5413), Acidovorax sp. TN-51 (FERM BP-5416), Pseudomonas sp. TN-131 (FERM BP-5418), Paracoccus sp. KK-6 (FERM BP-5415), Paracoccus sp. TNO-5 (FERM BP-6547), Sphingomonas sp. TN-28 (FERM BP-5419), Brevundimonas sp. TN-30 (FERM BP-5417) and Brevundimonas sp. TN-3 (FERM BP-5886), and further, transformants obtained by using *Escherichia coli* JM109 [*Escherichia coli* ATCC 53323] or *Rhodococcus rhodochrous* ATCC 17895 as a host.

Among the above-mentioned microorganisms, the strains KK-5, KK-9, TN-51, TN-131, KK-6, TN-28, TN-30, and TN-3 were newly isolated from the natural world by the present inventors and have been deposited with National Institute of Bioscience and Human Technology, Agency of Industrial Science and Technology, Ministry of International Trade and Industry (Higashi-1-1-3, Tsukuba-shi, Ibaraki-ken, Japan (postal code number 305-8566)) under the above-mentioned accession numbers according to Budapest treaty on the International Recognition of the Deposit of Microorganisms for the Purposes of Patent Procedure (hereinafter referred to Budapest Treaty). The mycological properties of these strains are described in the above-mentioned JPA-9-140390, JPA-10-52292, etc.

The strain TNO-5 was also newly isolated from the natural world by the present inventors and has been deposited with the above-mentioned National Institute of Bioscience and Human Technology, Agency of Industrial Science and Technology, Ministry of International Trade and Industry under the above-mentioned accession number according to Budapest treaty. Bacteriological properties thereof are as follows.

Bacteriological Properties of TNO-5 Strain

| Morphology | spherical-short bacillus |
|---|---|
| Gram staining | − |
| Spore | − |
| Motility | − |
| Attitude to oxygen | aerobic |
| Oxidase | + |
| Catalase | + |
| OF test | − |
| Color of colony | forming no characteristic pigment |
| Accumulation of PHB | + |
| Reduction of nitrate | − |
| Reduction of nitrite | − |
| Quinone type | Q-10 |
| GC content of DNA (mol %) | 65 (HPLC method) |

As a result of classification based on the above-mentioned bacteriological properties according to the description given in Bergey's Manual of Systematic Bacteriology, Vol. 1 (1984), the strain TNO-05 was identified as a bacterium belonging to the genus Paracoccus. Incidentally, it has been confirmed that the strain TN-3 belongs to diminuta sp.

The strain *Esherichia coli* JM109 (*Esherichia coli* ATCC 53323 strain) and the strain *Rhodococcus rhodochrous* ATCC 17895 are known and are easily available from the American Type Culture Collection (ATCC). Transformants obtained by using these strains as a host and introducing thereinto plasmids pEDS020 and pSE001 containing gene DNA which codes a protein having the EDDS-ase activity of the strain TN-3 have been deposited as *E. coli* JM109/pEDS020 (FERM BP-6161) and *Rhodococcus rhodochrous* ATCC17895/pSE001 (FERM BP-6548) with the above-mentioned National Institute of Bioscience and Human Technology, Agency of Industrial Science and Technology, Ministry of International Trade and Industry respectively under the above-mentioned accession numbers according to Budapest Treaty. Methods for preparation of these transformants are described in detail in JP-A-10-210984 filed by the present applicant.

The kind of the culture media for the microorganism used in the present invention are not particularly limited, and a synthetic medium or a natural medium may be used as long as it appropriately contains an assimilable carbon source, nitrogen source, inorganic salt and further a slight amount of an organic nutriment, etc. At the time of cultivation, it is preferable to add an amino acid, such as ethylenediamine-N,N'-disuccinic acid, ethylenediamine-N-monosuccinic acid, aspartic acid, glutamic acid and histidine, or fumaric acid and the like to the culture medium because thereby intended strain cells having a high activity may be obtained. Though the culture conditions may vary depending on the strain cells and the culture medium, the cultivation may be aerobically conducted at a pH range of the medium of from 4 to 10, preferably from 6 to 9 and a culture temperature range of from 20 to 45° C., preferably from 25 to 35° C. for from 1 to 10 days until the activity reaches the maximum.

The present invention is described in detail below with reference to Examples.

EXAMPLE 1

(1) Preparation of Strain Cell Catalyst

One platinum loop of *Esherichia coli* JM109/pEDS020 was taken out from a slant culture, inoculated into an LB culture medium (1% bacto-tripton, 0.5% bacto-yeast extract, 0.5% NaCl) containing 50 mg/l of ampicillin and subjected to a cultivation with shaking at 37° C. for 8 hours. The resulting culture broth was inoculated in an amount of 2.5% into an LB culture medium (containing 50 mg/l ampicillin, 1 mM of isopropyl-β-thiogalactoside) and subjected to an aerobic cultivation with shaking at 37° C. for 30 hours. From 1000 ml of the resulting culture solution, the strain cells were harvested by centrifugation (7,000 rpm, 20 min.) and washed once with 500 ml of 50 mM borate buffer solution (pH 7.75) containing 100 mM of 1,4-diaminobutane. The strain cells were resuspended in 500 ml of a similar buffer solution and then, in an ice bath, 25% glutaraldehyde was gradually added to the suspension so as to reach a concentration of 25 mM. Since the pH decreased during the time, the pH was adjusted to 7.75 with 6N NaOH and then the suspension was allowed to stand with stirring for 2 hours. Ethylenediamine was then added to the suspension so as to reach a concentration of 50 mM, the pH was adjusted to 9.0 with 6N NaOH, and the suspension was allowed to stand for 2 hours. Then sodium borohydride was added so as to reach a concentration of 25 mM and the resulting suspension was allowed to stand with stirring for further two hours. Then the suspension was adjusted to pH 9.2 with 6N NaOH and then heat-treated in a water bath at 45° C. for 4 hours to obtain a strain cell suspension freed of fumarase activity.

(2) Preparation of Reaction Mixture and Reaction

Fumaric acid, magnesium hydroxide and ethylenediamine were added, in the above-mentioned order, to water with vigorous stirring so that the concentrations of the respective components at the start of the reaction might be 1,027 mM of fumaric acid, 513 mM of ethylenediamine and 770 mM of magnesium hydroxide, to obtain a transparent reaction mixture. The above-mentioned strain cell suspension was added to the reaction mixture, and the resulting mixture was allowed to react at 40° C. with stirring.

Since the pH of the mixture would decrease with the progress of the reaction, pH was kept at 8.5 by feeding, as required, a NaOH solution with a pH controller. The amount of SS-EDDS formed with the progress of the reaction was determined with the lapse of time. Resultantly, the concentration of the SS-EDDS formed after 24 hours was found to be 468 mM.

The method for determination of SS-EDDS concentration is as follows.

After removing insoluble matters in the reaction product mixture by means of centrifugation at 15,000 rpm for 5 min. at 5° C., SS-EDDS was determined by liquid chromatography. An column for determination used was WAKOSIL 5C8 (Wako Pure Chemical Industries, Ltd., Japan) (eluent: 50 mM phosphoric acid containing 10 mM of tetra-n-butylammonium hydroxide and 0.4 mM of $CuSO_4$, pH 2) and an optical resolution column used was MCI GEL CRS 10W (mfd. by Mitsubishi Chemicals Ltd., Japan) (eluent: 10 mM $CuSO_4$).

(3) Insolubilization and Recovery of Magnesium Ion

To a transparent reaction product mixture, from which the strain cells had been removed by a centrifugation (15,000 rpm, 5 min.), was added 7.5N NaOH so as to be 3 times by mole and 4 times by mole relative to the SS-EDDS concentration, and the resulting mixtures were allowed to stand with stirring at room temperature for 1 hour. The precipitate of magnesium ion origin thus formed was removed by centrifugation (15,000 rpm, 5 min.). Resultantly, the percentages of removal of magnesium ion were found to be 61% and 95%, respectively, the particle diameters were both not more than 7 μm, and the average particle diameters were 1.3 and 1.6 μm, respectively.

(4) Reuse of Recovered Magnesium

By using the recovered magnesium precipitate, a reaction mixture was prepared according to the procedure described in above (2). The concentrations of the respective components at the start of the reaction were 1,027 mM of fumaric acid, 513 mM of ethylenediamine, 770 mM (in terms of magnesium) of recovered magnesium, 72 mM of SS-EDDS and 10 g/l of the strain cells in terms of dry weight, and the pH actually determined was about 8.8. Reaction was conducted in the same manner as above (2).

As the result, no significant difference was observed in the reaction velocity, and the SS-EDDS concentration after 24 hours was 540 mM.

EXAMPLE 2

(1) Preparation of Strain Cell Catalyst

A strain cell suspension was prepared in the same manner as in Example 1.

(2) Preparation of Reaction Mixture and Reaction

A reaction mixture was prepared in the same manner as in Example 1 provided that iron (III) hydroxide was used in place of magnesium hydroxide, and was adjusted to pH 7.5 by using 7.5N NaOH. At the start of the reaction, the concentrations of fumaric acid, ethylenediamine and the strain cells were respectively the same as in Example 1 and the concentration of iron (III) hydroxide was 513 mM. At this time, the iron (III) oxide dissolved only partly in the reaction mixture solution.

During the reaction, since the pH increased with the progress of reaction unlike in the case of using magnesium hydroxide, pH adjustment was done by using 5N sulfuric acid. As the result, the concentration of the SS-EDDS formed after 24 hours was 449 mM.

(3) Insolubilization and Recovery of Iron (III) Ion

To a transparent supernatant obtained by removing the strain cells by a centrifugation was added in the same manner as in Example 1 7.5N NaOH so as to be 4 times by mole relative to the SS-EDDS concentration to insolubilize and recover the iron (III) ion. The percentage removal of iron (III) ion was 98%.

(4) Reuse of Recovered Iron (III)

A reaction mixture was prepared according to a similar procedure to that in above (2) by using the recovered precipitate. The concentrations of the respective components at the start of the reaction were 1,027 mM of fumaric acid, 513 mM of ethylenediamine, 513 mM of recovered iron (III) (concentration in terms of iron), 86 mM of SS-EDDS and 10 g/l of the strain cells in terms of dry weight, and the reaction was carried out in the same manner as in above (2).

As the result, no significant difference was observed in the reaction velocity, and the SS-EDDS concentration after 24 hours was 530 mM.

EXAMPLE 3

(1) Preparation of Strain Cell Catalyst

A strain cell suspension was prepared in the same manner as in Example 1.

(2) Preparation of Reaction Mixture and Reaction

A reaction mixture was prepared and reaction was conducted in the same manner as in Example 2 except for using an equal mole concentration of manganese (II) hydroxide in place of iron (III) hydroxide. As the result, the concentration of SS-EDDS formed after 24 hours was 428 mM.

(3) Insolubilization and Recovery of Manganese (II)

Manganese (II) was insolubilized and recovered in the same manner as in Example 2. The percentage removal of manganese (II) ion was 97%.

(4) Reuse of Recovered Manganese (II)

A reaction mixture was prepared according to a similar procedure to that in above (2), by using the recovered precipitate. The concentrations of the respective components at the start of reaction were 1,027 mM of fumaric acid, 513 mM of ethylenediamine, 513 mM of recovered manganese (II) (concentration in terms of manganese), 52 mM of SS-EDDS and 10 g/l of the strain cells in terms of dry weight, and the reaction was conducted in the same manner as in above (2).

As the result, no significant difference was observed in the reaction velocity and the SS-EDDS concentration after 24 hours was 480 mM.

EXAMPLE 4

(1) Preparation of Strain Cell Catalyst

A strain cell suspension was prepared in the same manner as in Example 1.

(2) Preparation of Reaction Mixture and Reaction

The same operations as in Example 1 were conducted except for using 7.5N KOH in place of 7.5N NaOH as the alkali for pH control. The concentration of SS-EDDS formed after 24 hours was 472 mM.

(3) Insolubilization and Recovery of Magnesium Ion

To a transparent reaction product mixture, from which the strain cells had been removed by centrifugation (15,000 rpm, 5 min.), was added 7.5N KOH so as to be 4 times by mole relative to the SS-EDDS concentration, and the resulting mixture was allowed to stand with stirring at room temperature for 1 hour. The precipitate of magnesium ion origin thus formed was removed by centrifugation (15,000 rpm, 5 min.) to find that the percentage removal of magnesium ion was 95%.

(4) Reuse of Recovered Magnesium

A reaction mixture was prepared according to a similar procedure to that in above (2) but by using the recovered precipitate of magnesium. The concentrations of the respective components at the start of reaction were 1,027 mM of fumaric acid, 513 mM of ethylenediamine, 770 mM of recovered magnesium (concentration in terms of magnesium), 82 mM of SS-EDDS and 10 g/l of the strain cells in terms of dry weight, and the pH actually determined was about 8.9. The reaction was conducted in the same manner as above (2).

As the result, no significant difference was observed in the reaction velocity, and the SS-EDDS concentration after 24 hours was 546 mM.

EXAMPLE 5

(1) Preparation of Strain Cell Catalyst

A strain cell suspension was prepared in the same manner as in Example 1.

(2) Preparation of Reaction Mixture and Reaction

A reaction was conducted in the same manner as in Example 1.

(3) Insolubilization and Recovery of Magnesium Ion

To a transparent reaction product mixture (pH 8.7), from which the strain cells had been removed by centrifugation (15,000 rpm, 5 min.), was added 7.5N NaOH so as to be 2, 2.5, 3, 3.5 and 4 times by mole relative to the SS-EDDS concentration, the resulting pH being 10.6, 11.7, 11.9, 12.1 and 12.5, respectively, and the resulting mixtures were allowed to stand with stirring at 40° C. overnight. The precipitates of magnesium ion origin thus formed were removed by centrifugation (6,000 rpm, 5 min.) to find that the percentages of removal of magnesium ion were 11%, 29%, 50%, 74% and 96%, respectively.

EXAMPLE 6

(1) Preparation of Strain Cell Catalyst

A strain cell suspension was prepared in the same manner as in Example 1.

(2) Preparation of Reaction Mixture and Reaction

A reaction was conducted in the same manner as in Example 1.

(3) Insolubilization and Recovery of Magnesium Ion

To a transparent reaction product mixture (pH 8.9), from which the strain cells had been removed by centrifugation (15,000 rpm, 5 min.), was added 7.5N NaOH so as to be 2, 2.5, 3, 3.5, and 4 times by mole relative to the SS-EDDS concentration, the resulting pH being 10.9, 11.9, 12.1, 12.3 and 12.7, respectively, and the resulting mixtures were allowed to stand with stirring at 20° C. overnight. The precipitates of magnesium ion origin thus formed were removed by centrifugation (6,000 rpm, 5 min.) to find that the percentages of removal of magnesium ion were 8%, 29%, 49%, 74% and 97%, respectively.

EXAMPLE 7

(1) Preparation of Strain Cell Catalyst

A strain cell suspension was prepared in the same manner as in Example 1.

(2) Preparation of Reaction Mixture and Reaction

A reaction was conducted in the same manner as in Example 1.

(3) Insolubilization and Recovery of Magnesium Ion

To 680 ml of water at 40° C. were added together a transparent reaction product mixture, from which the strain cells had been removed by centrifugation (1,500 rpm, 5 min.), and 7.5N NaOH so as to be 4.2 times by mole relative to the SS-EDDS concentration. Simultaneously therewith, the slurry of the precipitate formed was continuously withdrawn so as to give a residence time of 2 hours. After the lapse of 14 hours from the beginning of feeding and withdrawing, a part of the slurry was sampled and the precipitate was removed therefrom by centrifugation (6,000 rpm, 5 min.) to find that the percentage removal of magnesium ion was 99.3%. At this time, the pH of the slurry was 13.1 and the slurry concentration was 2.3% by weight. The precipitate of magnesium origin had particle diameters in the range from 1 μm to 130 μm and average particle diameter of 45 μm.

EXAMPLE 8

(1) Preparation of Strain Cell Catalyst

A strain cell suspension was prepared in the same manner as in Example 1.

(2) Preparation of Reaction Mixture and Reaction

A reaction was conducted in the same manner as in Example 1.

(3) Insolubilization and Recovery of Magnesium Ion

The same operations as in Example 7 were performed except for changing the amount of 7.5N NaOH fed together with the reaction mixture to 3.5 times by mole relative to the SS-EDDS concentration. After the lapse of 14 hours from the beginning of feeding and withdrawing, a part of the slurry was sampled and the precipitate was removed therefrom by centrifugation (6,000 rpm, 5 min.) to find that the percentage removal of magnesium ion was 77%. At this time, the pH of the slurry was 12.1 and the slurry concentration was 1.9% by weight. The precipitate of magnesium origin had an average particle diameter of 27 μm.

INDUSTRIAL APPLICABILITY

According to the present invention, by adding an alkali hydroxide to the reaction product mixture, SS-EDDS metal complex can be converted to SS-EDDS alkali metal salt, at the same time the metal ion used for the reaction can be recovered as a precipitate and furthermore the recovered precipitate can be reused as the metal ion source, so that an SS-EDDS alkali metal salt can be produced with good efficiency in respect of reaction velocity, yield, operation, cost, etc. [S,S]-ethylenediamine-N,N'-disuccinic acid is a compound expectedly useful as a biodegradable chelating agent for use in such fields as photography, detergents and paper making.

What is claimed is:

1. A process for producing an [S,S]-ethylenediamine-N,N'-disuccinic acid alkali metal salt which comprises reacting fumaric acid with ethylenediamine in an aqueous medium in the presence of an ion of at least one metal selected from the group consisting of alkaline earth metals and transition metals by the action of ethylenediamine-disuccinic acid ethylenediamine lyase of microorganism origin, adding an alkali hydroxide to a reaction product mixture thereby to separate and recover the metal ion as an insoluble precipitate, and obtaining an [S,S]-ethylenediamine-N,N'-disuccinic acid alkali metal salt.

2. The process according to claim 1 wherein the separated and recovered insoluble precipitate is reused as a source of the metal ion in the production of [S,S]-ethylenediamine-N,N'-disuccinic acid.

3. The process according to claim 1 wherein the reaction product mixture and the alkali hydroxide are fed together.

4. The process according to claim 3 wherein a slurry is withdrawn simultaneously with feeding the reaction product mixture and the alkali hydroxide together.

5. The process according to claim 1 wherein the alkaline earth metal is magnesium and the transition metals are manganese and iron.

6. The process according to claim 2, wherein the reaction product mixture and the alkali hydroxide are fed together.

* * * * *